United States Patent [19]
Ambrus et al.

[11] Patent Number: 5,276,044
[45] Date of Patent: Jan. 4, 1994

[54] LEUKOTRIENE RECEPTOR ANTAGONIST AND ANTIHISTAMINE COMPLEX PHARMACEUTICAL COMPOSITIONS

[75] Inventors: Gyorgy F. Ambrus, Tustin, Calif.; Kenneth J. Himmelstein, Pearl River, N.Y.; David F. Woodward, El Toro, Calif.

[73] Assignee: Allergan, Inc., Irvine, Calif.

[21] Appl. No.: 745,232

[22] Filed: Aug. 14, 1991

[51] Int. Cl.$^5$ .................... A61K 31/44; A61K 31/19
[52] U.S. Cl. .................... 514/352; 514/570
[58] Field of Search ............... 514/329, 352, 826, 570

[56] References Cited

U.S. PATENT DOCUMENTS 4,623,535 11/1986 Perchonock .................... 424/43
4,683,325 7/1987 Frenette et al. .................. 560/10

FOREIGN PATENT DOCUMENTS 0233763 8/1987 European Pat. Off.
0433766A1 6/1991 European Pat. Off.

OTHER PUBLICATIONS

Merck Index, Eleventh Edition, p. 1270, #7996 (1989).
Reprint from Journal of Medicinal Chemistry, vol. 30, No. 6, Jun. 1987, entitled "Communications to the Editor".
"Synthesis and Structure-Activity Relationship Studies of a Series of 5-Aryl-4, 6-dithianonanedioic Acids and Related Compounds: Novel Class of Leukotriene Antagonists", J. Med. Chem. 1986, 29, 1442-1452, C. D. Perchonock et al.
"Antagonists of Slow-Reacting Substance of Anaphylaxis, 1. Pyrido[2,1-b] quinazolinecarboxylic Acid Derivatives", J. Med. Chem., 1983, 26, 1638-1642, J. W. Tilley, et al.
"Leukotriene Receptor Antagonists 1. Synthesis and Structure-Activity Relationships of Alkoxyacetophenone Derivatives", J. Med. Chem. 1987, 30, 682-689, W. S. Marshall, et al.
"Antagonism of the in vivo and in vitro effects of leukotriene D$_4$ by SC-39070 in guinea pigs", Agents and Actions, vol. 20, 2$3 (1987), G. W. Carnathan, et al.
Pp. 695, 697, 805 and 807 from "Drugs of the Future", vol. 15 Nos. 7 and 8, 1990.
"Interactive effects of peptidoleukotrienes and histamine on microvascular permeability and their involvement in experimental cutaneous and conjunctival immediate hypersensitivity", European Journal of Pharmacology, (1989) 323-333, D. F. Woodward, et al.
"5-Lipoxygenase inhibitors and allergic conjunctivitis reactions in guinea-pig", European Journal of Pharmacology, 143, (1987) 1-7, D. Garceau et al.
"Pharmacology of Histamine Receptors"; C. R. Ganellin, et al Wright P. S. G., 1982 (pp. 60-62).
Pp. 736-739; "Drugs of the Future", vol. VII, No. 10 1982 (S. J. Hopkins).
Pp. 695 & 697 "Drugs of the Future", vol. 15, No. 7, 1990 & pp. 805 & 807, vol. 15, No. 8, 1990.
"Communications to the Editor", Journal of Medicinal Chemistry, 1987, vol. 30, No. 6, pp. 959-961.
Fishleder, et al., "An examination of the ability of dtubocurarine to evoke contraction and mediator release from superfused trachea adn parenchymal strips isolated from the guinea pig", J. Pharmacol. Exp. Ther., (8/87), 242(2), 558-565.
V. B. Weg, et al., "Histamine, leukotriene D4 and plactelet-activating factor in guinea pig passive cutaneous anaphylaxis", Eur. J. Pharmacol. 1991, 204(2), 157-163.
Schachter, et al., "Pharmacologic studies of cotton bract extract in isolated guinea pig trachea", Cotton Dust, 1988, 12th, 90-1.

Primary Examiner—Frederick E. Waddell
Assistant Examiner—T. J. Criares
Attorney, Agent, or Firm—Poms, Smith, Lande & Rose

[57] ABSTRACT

Pharmaceutical compositions are disclosed which effectively treat the symptoms of hypersensitivity diseases without irritation. The pharmaceutical compositions are complexes of at least one leukotriene receptor antagonist and at least one antihistamine. The complexes can be formulated in low viscosity solutions for administering to an individual as an aerosol or drops or through intravenous, subcutaneous, or intramuscular injection. Alternatively, the complexes can be formulated in high viscosity creams for topical delivery to the skin or ocular environment.

7 Claims, No Drawings

LEUKOTRIENE RECEPTOR ANTAGONIST AND ANTIHISTAMINE COMPLEX PHARMACEUTICAL COMPOSITIONS

FIELD OF THE INVENTION

The present invention relates in general to pharmaceutical compositions useful for treating hypersensitivity diseases. More particularly, the present invention is directed toward complexes formed from leukotriene receptor antagonists and antihistamines. These complexes suppress the symptoms of hypersensitivity diseases with a high degree of activity, yet are unusually nonirritating, making them particularly suitable for the treatment of allergic conjunctivitis, hay fever, and asthma.

BACKGROUND OF THE INVENTION

Immediate hypersensitivity diseases, including asthma, hay fever, and allergic conjunctivitis are associated with a variety of unpleasant symptoms including tearing, inflammation, and breathing difficulty. The physiological mechanisms which promote these symptoms are similar for all hypersensitivity diseases and generally are initiated by environmental antigens. Patients suffering from the effects of hypersensitivity diseases are predisposed to specific external antigens. When these antigens contact certain tissues such as ocular, nasal, or lung tissues, these tissues become sensitized and produce undesirable and frequently life-threatening symptoms.

Allergic conjunctivitis in particular can be an extremely debilitating disease for children. While the response to allergic conjunctivitis may be limited to mild tearing and red-eyes, the much more severe form of vernal conjunctivitis is very common among children with this disease. Vernal conjunctivitis produces such serious responses as severely swollen eyelids, and extremely irritated and itching eyes to the point where it adversely effects the quality and the way of life of those having the disease. The discomfort is frequently so great that children suffering from the vernal conjunctivitis are unable to sleep or participate in school activities.

Traditionally, the preferred treatment for hypersensitivity diseases has involved the use of antihistamines. Unfortunately, antihistamines alone do not entirely abolish the adverse symptoms of these diseases and more efficacious forms of therapy are needed, particularly for the treatment of allergic conjunctivitis. Other treatment forms have found limited success but each of them has associated disadvantages as well.

Among these treatment forms are vasoconstrictors which take away the red eye component of allergic conjunctivitis. These are limited in their usefulness because once they are discontinued the symptoms reappear in a more severe form. These drugs are unpopular with physicians largely due to this rebound phenomenon. Another drug which has received attention for the treatment of allergic conjunctivitis is disodium cromoglycate, a mast cell stabilizer. Disodium cromoglycate has received regulatory approval for at least one indication; however, it has not proven to be particularly efficacious. Alternatively, glucocorticoids provide relief from the symptoms of hypersensitivity diseases, yet physicians are reluctant to prescribe them because of their side effects.

Researchers and clinicians have long known the importance of both a histaminergic component and a nonhistaminergic component to hypersensitivity diseases. Antihistamines serve as antagonists for the mediators of the histaminergic component; however, it is now generally accepted that to effectively treat these diseases mediators of both components must be suppressed.

A class of compounds known as leukotrienes are known to mediate the nonhistaminergic component, but it was not until the early 1980's that researchers were able to isolate and identify these compounds. Since then a large number of possible leukotriene antagonists have been identified, synthesized, and tested. In *Synthesis and Structure—Activity Relationship Studies of a Series of 5-Aryl-4,6-dithianonanedioic Acids and Related Compounds: A Novel Class of Leukotriene Antagonists*, J. Med. Chem. 29, 1442–1452, 1986, Perchonock, et al. discuss the leukotriene antagonist activity of the title compounds. Similarly in *Communications to the Editor*, Journal of Medicinal Chemistry, 30. 959–961, 1987, Gleason, et al. disclose the high affinity leukotriene receptor antagonist activity of 2-hydroxy-3-[(2-carboxymethyl)thio]-3-[-2-(8-phenyloctyl)phenyl]propanoic acid.

When these leukotriene antagonists are tested in animal models they do, in fact, partially block the adverse symptoms associated with hypersensitivity diseases. Furthermore when an antihistamine and a leukotriene antagonist are both administered to sensitized animals, the combination results in a near complete suppression of the symptoms. The test results confirm the theory that if both the histaminergic mediator and nonhistaminergic mediator of the hypersensitivity disease are effectively antagonized, the treatment is more efficacious than blocking a single mediator.

Unfortunately, the above leukotriene receptor antagonists have proven to be extreme tissue irritants. This irritating characteristic is attributed to long chain carboxylate functionalities which give the compounds a detergent like structure. This precludes the utility of these compounds for direct application to the eye, nasal, or bronchial passages. It is further known that the insoluble zinc and poorly soluble calcium salts of leukotriene antagonists are less irritating, because it is believed they do not ionize to form the detergent-like free carboxylate functionalities. However, these salts are not as effective at treating the nonhistaminergic component of hypersensitivity diseases and are incompatible with the soluble antihistamine hydrochlorides which are effective in blocking the histaminergic component. Thus, for purposes of providing a complete formulation for safely and effectively blocking both the histaminergic and nonhistaminergic components of hypersensitivity diseases, the insoluble salts in combination with an antihistamine do not provide a workable solution.

Accordingly, it is an object of the present invention to provide an effective pharmaceutical composition which significantly suppresses the adverse symptoms associated with hypersensitivity diseases.

It is a further object of the present invention to provide a single formulation pharmaceutical composition for effectively treating hypersensitivity diseases without causing irritation of ocular, nasal or lung tissue.

It is an additional object of the present invention to provide pharmaceutical compositions which can be conveniently administered in a variety of delivery forms for the effective treatment of hypersensitivity diseases.

SUMMARY OF THE INVENTION

Generally stated, the present invention accomplishes the above-described objectives by providing pharmaceutical compositions which effectively suppress the adverse symptoms associated with the different components of hypersensitivity diseases. Moreover, the pharmaceutical compositions of the present invention can be formulated in single treatment forms and administered to tissue sites without the discomfort and irritation associated with the prior art therapeutic compositions. What is more, the pharmaceutical compositions of the present invention may be formulated to incorporate a wide variety of pharmaceutically acceptable carriers to accommodate a variety of delivery forms which range from heavy creams to light aerosols.

More particularly, the pharmaceutical compositions of the present invention are novel complexes of at least one leukotriene receptor antagonist and at least one antihistamine. The combination of leukotriene receptor antagonist and an antihistamine provides a single complex for effectively treating both the histaminergic component and the nonhistaminergic component of hypersensitivity diseases. A particularly advantageous and unexpected feature of the pharmaceutical compositions of the present invention is the absence of tissue irritation typically associated with leukotriene receptor antagonists when they are delivered to tissue sites in their uncomplexed form.

In accordance with the teachings of the present invention, the complex of leukotriene receptor antagonist and antihistamine can be formulated to include a variety of different pharmaceutically acceptable carriers. These carriers effectively dissolve the complex of leukotriene receptor antagonist and antihistamine without dissociating the complex, thereby preserving its nonirritating properties. Furthermore, the pharmaceutical compositions of the present invention can be administered to a variety of tissue sites using a number of different delivery forms by choosing a pharmaceutically acceptable carrier having the appropriate flow properties. As those skilled in the art will appreciate, the treatment of hypersensitivity diseases involves delivery forms which vary from viscous creams for topical applications for the skin, to aqueous solutions for the eye, to light aerosols for use in inhalers. The advantageous solubility properties of the complex of leukotriene receptor antagonist and antihistamine allow the pharmaceutical compositions of the present invention to be administered in any delivery form without causing irritation to tissue.

As will be discussed below, a wide variety of leukotriene receptor antagonists and antihistamines may be utilized to form the complexes which comprise the pharmaceutical compositions of the present invention. Preferably the complex of leukotriene receptor antagonist and antihistamine is an acid-base complex with the leukotriene receptor antagonist having at least one acid functionality and the antihistamine having at least one base functionality. The acid base complexes utilized in the pharmaceutical compositions of the present invention are prepared by methods known in the art for forming complexes of weak acids and weak bases. These methods include conventional separation and purification techniques.

Further objects and advantages of the pharmaceutical compositions of the present invention, as well as a better understanding thereof, will be afforded to those skilled in the art from a consideration of the following detailed explanation of preferred exemplary embodiments thereof.

DETAILED DESCRIPTION OF PREFERRED EMBODIMENTS

In a broad aspect, the pharmaceutical compositions of the present invention comprise a complex of at least one leukotriene receptor antagonist and at least one antihistamine. This complex is useful for the effective treatment of hypersensitivity diseases such as asthma, hay fever and allergic conjunctivitis. Moreover, because of the unexpected non-irritating nature of the complex, the pharmaceutical compositions of the present invention are particularly well suited for use as a single formulation in the treatment of allergic conjunctivitis in which the pharmaceutical compositions are delivered via topical applications to the ocular environment. However, those skilled in the art will appreciate that the pharmaceutical compositions of the present invention are also well-suited for delivery to bronchial tissue using aerosols, to nasal passages using aerosols and drops, to intravenous delivery, and to transdermal delivery through topical application to the skin.

Many leukotriene receptor antagonists contain at least one acid functionality and antihistamines contain at least one base functionality. Accordingly, for purposes of explanation and without limiting the scope of the present invention, the pharmaceutical compositions of the present invention will be discussed in the context of acid-base complexes of leukotriene receptor antagonists having at least one acid functionality and antihistamines having at least one base functionality. More particularly, an exemplary nonirritating pharmaceutical composition having enhanced activity for the treatment of hypersensitivity diseases produced in accordance with the teachings of the present invention comprises a therapeutically effective amount of a complex of a leukotriene receptor antagonist and an antihistamine. In the preferred embodiments of the present invention, the complex is an acid-base complex. The molar ratio of leukotriene receptor antagonist to antihistamine in the acid-base complex is generally dependent upon the ratio of acid functionalities present in the leukotriene receptor antagonist to basic functionalities present in the antihistamine. However, this molar ratio is also dependent upon the relative strength of the acid and base functionalities as well as certain steric considerations.

Exemplary leukotriene receptor antagonists suitable for use in the acid-base complexes include those having the general formula:

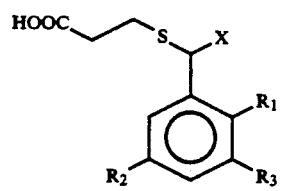

wherein $R_1$ is H, alkyl of 10–12 carbons, monoalkenes of 10–12 carbons alkylphenyl of 8 alkyl carbons, alkyl ethers of 9 to 11 alkyl carbons, thio alkyl ether of 11 alkyl carbons or alkylphenyl ethers of 6 to 8 alkyl carbons; $R_2$ is H, —OH, —OCH$_3$, —Br, —NO$_3$, or —CF$_3$; X is —SC$_2$H$_4$COOH, or —CHOHCOOH; and $R_3$ is alkyl phenyl of 8–10 alkyl carbons, alkyl ethers of 9–11 alkyl carbons, or alkene ethers of 9 to 11 carbons.

Other recognized leukotriene receptor antagonists which are suitable for use in producing the pharmaceutical compositions of the present invention include those having the following structures:

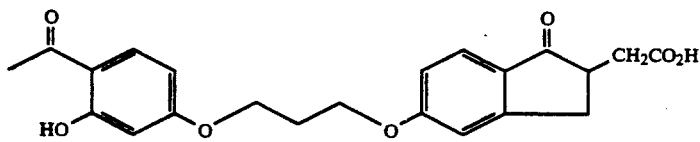

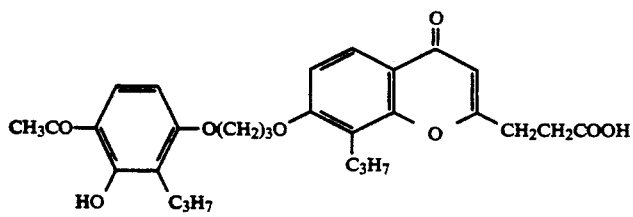

The leukotriene receptor antagonists having the above identified structures and formulas have a hydrophilic portion characterized by the carboxylic acid functionalities, and a lipophilic portion characterized by the alkyl and aryl functionalities. This structure gives these leukotriene receptor antagonists a detergent-like property which is responsible for their tendency to burn and irritate tissue.

Antihistamines which are particularly suitable for use in the pharmaceutical compositions of the present invention include pyrilamine, mepyramine, tripelennamine, cyclizine, chlorcyclizine, promethazine, fenethazine, diphenhydramine, diphenylpyraline, pheniramine, chlorpheniramine, triprolidine, pyrrobutamine, and phenindamine. Each of the above antihistamines provides at least one amine base functionality for complexing with a leukotriene receptor antagonist having at least one acid functionality.

In accordance with the teachings of the present invention, a preferred exemplary pharmaceutical composition for treating hypersensitivity diseases comprises a pharmaceutically effective amount of an acid-base complex of 2(S)-hydroxy3(R)-[(2-carboxyethyl)thiol -3-[-2-(8-phenyloctyl)phenyl]propionic acid and pyrilamine. This complex has the following formula:

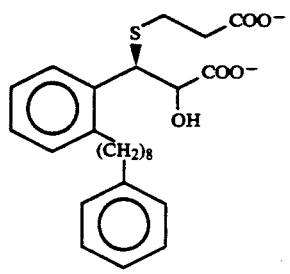

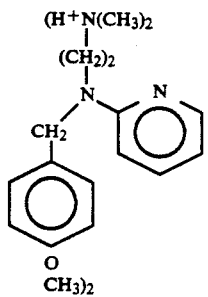

The pharmaceutical compositions of the present invention can be produced using a variety of methods known in the art. For example, simply forming a solution of at least one leukotriene receptor antagonist and at least one antihistamine in a suitable solvent or solvent mixture will form a complex of the leukotriene receptor antagonist and the antihistamine. Suitable solvents or solvent mixtures are those which dissolve the leukotriene receptor antagonist and the antihistamine. Additionally, the solvent should not interfere with the formation of the complex. Additionally, if desired, separating the solvent using known separation techniques produces a concentrated complex of the antihistamine and leukotriene receptor antagonist. This complex can be incorporated into pharmaceutically acceptable carriers at concentrations of from about 0.001 wt. % to about 10.0 wt. % to form pharmaceutical compositions which are convenient for administering through a variety of techniques. Adding water to the complex and carrier medium is also possible when lower viscosity pharmaceutical compositions are required for different forms of administration or delivery.

Alternatively, a complex of leukotriene receptor antagonist and antihistamine can be prepared using conventional titration techniques. For example, forming a first solution of an antihistamine in a pharmaceutically acceptable solvent or solvent mixture and a second solution of a leukotriene receptor antagonist in the same pharmaceutically acceptable solvent or mixture of solvents and titrating or adding the antihistamine solution to the leukotriene receptor antagonist solution while monitoring the pH of the leukotriene receptor antagonist solution. Suitable pharmaceutically acceptable solvents include water, polysorbates, polyethylene glycols and polyethylene glycol sorbates.

When the pH is raised to the point at which all carboxylate functionalities are blocked in an acid-base complex, the reaction is complete. Preferably a 5% excess of antihistamine is added to the final solution to assure that all the carboxylate functionalities are completely blocked. This excess allows for a higher than theoretical amount of the antihistamine required to titrate the entire amount of leukotriene antagonist. This exemplary titration method also provides for the direct preparation of the acid base complex without subsequently removing the solvent. Additional water and/or cosolvent can be added to vary the concentration of the complex, if desired.

It is also contemplated to be within the scope of the present invention to provide pharmaceutical compositions for the treatment of hypersensitivity diseases comprising a therapeutically effective amount of such complexes and at least one pharmaceutically acceptable carrier. Accordingly, pharmaceutical compositions produced from a pharmaceutically acceptable carrier and a complex of a leukotriene receptor antagonist and an antihistamine can be formulated to be administered in a variety of forms. In accordance with the present invention these forms can vary from viscous creams for topical applications to freely flowing compositions for use with inhalers.

Preferably the pharmaceutically acceptable carrier has an aqueous base and contains one or more cosolvents capable of providing a homogeneous pharmaceutical composition. Suitable cosolvents are polyethylene glycols, polysorbates, polysorbate stearates, polyvinylalcohols, and polyvinylpyrrolidones. For most applications, the pharmaceutically acceptable carrier will have an aqueous base; however, it is within the scope of the present invention to provide pharmaceutical compositions having a carrier comprising cosolvents without added water.

In accordance with the teachings of the present invention, when the pharmaceutical compositions of the present invention include one or more pharmaceutically acceptable carriers, the complex of leukotriene receptor antagonist and antihistamine is present at a concentration of from approximately 0.001% by wt. to 10.0% by wt. The preferred concentration depends upon the antihypersensitivity activity of the complex, the nature of the hypersensitivity disease being treated, and the method of administering the pharmaceutical composition. However, the pharmacological activity of the pharmaceutical compositions of the present invention is extremely high. Accordingly, effective concentrations of the acid-base complex are correspondingly small.

The following non-limiting example illustrates a method for preparing a preferred embodiment of the present invention.

EXAMPLE 1

A complex of a leukotriene receptor antagonist having the formula 2(S)-hydroxy3(R)-[(2-carboxy-ethyl)-thiol -3-[-2-(8-phenyloctyl)phenyl]propionic acid disodium salt and the antihistamine pyrilamine was prepared according to the following procedure. 1.01 gm of the leukotriene receptor antagonist disodium salt was dissolved in 40 ml of purified water. The leukotriene receptor antagonist has a molecular weight of 502.6 which resulted in an aqueous solution of $2 \times 10^{-3}$ moles of leukotriene receptor antagonist. The pH of the leukotriene receptor antagonist was adjusted to 7.4 with $NaH_2PO_4 \cdot H_2O$ and $Na_2HPO_4 \cdot 7H_2O$.

A second solution of antihistamine was prepared by dissolving 1.52 grams of the pyrilamine HCl in 60 ml of purified water. The molecular weight of the pyrilamine hydrochloride is 321.9 which resulted in an aqueous solution of $4.7 \times 10^{-3}$ moles of pyrilamine. The pH of the solution was adjusted to 7.4 with $Na_2HPO_4 \cdot 7H_2O$.

Approximately 75% of the pyrilamine solution was slowly added to the leukotriene receptor antagonist solution. After 10–15 minutes an oily phase formed at the bottom of the flask. This oily phase contained the acid base complex. After 4 hours another 15% of the total pyrilamine solution was added to the leukotriene receptor antagonist solution. The final 10% of the total pyrilamine solution was added to the leukotriene receptor antagonist solution with no resulting increase in the oily phase which indicated that the complex formation was complete.

The oily phase was extracted with 35 ml of ethyl acetate followed by the vacuum removal of the ethyl acetate to produce a substantially pure complex of the leukotriene receptor antagonist and pyrilamine.

As mentioned above, in producing the pharmaceutical compositions of the present invention the leukotriene receptor antagonist and antihistamine form a complex which blocks the free carboxylic acid functionalities resulting in a non-irritating yet active antihypersensitivity compound. In general, the carboxylate functionalities are substantially blocked when stoichiometric amounts of acid and base are utilized. However, to assure complete blocking of the carboxylic acid functionalities, the base is preferably present in at least a 5% excess. Thus, in the method described in Example 1 above, the pyrilamine complexes with the leukotriene receptor antagonist in a 2:1 molar ratio but as much as 2.3 moles of the antihistamine was present in the solution for every mole of leukotriene receptor antagonist.

Another factor which should be considered in preparing the pharmaceutical compositions of the present invention, is the relative strength of the acid and base functionalities. As described above, one mole of leukotriene receptor antagonist having two acid functionalities will generally form an acid-base complex with two moles of an antihistamine having one basic functionality. However, those skilled in the art will appreciate that when the acid functionalities are only weakly acidic, stronger bases are required to block the acids. Thus, even though pyrilamine has 3 basic functionalities, only one is strong enough to complex with the relatively weakly acidic leukotriene receptor antagonist. Accordingly, the pharmaceutical compositions of the present invention can be formed of acid-base complexes having a variety of molar ratios of acid to base functionalities and the molar ratios are dependent upon the relative strengths of the acid and the base.

To facilitate the administration of the pharmaceutical compositions of the present invention, the complexes so formed may be incorporated into a variety of pharmaceutical carriers ranging from viscous creams to low viscosity liquids. The preferred carrier flow property will depend upon the method chosen for administering the pharmaceutical composition. For example, for purposes of treating allergic conjunctivitis, an exemplary acid-base complex can be incorporated in a viscous carrier medium to form a creme which is conveniently applied topically. In contrast, the pharmaceutical compositions can be formulated in aqueous carriers for use in aerosol inhalers, in intravenous injection solutions, and in nose or eye drops where appropriate. In order to formulate a pharmaceutical composition having the desired characteristics, the flow properties of the carrier should be varied by using the appropriate type of cosolvents and the appropriate amount of water as known in the art.

The following example is illustrative of the types of cosolvents which are suitable for use in the pharmaceutical composition of the present invention.

EXAMPLE 2

In order to determine the effect of certain pharmaceutically acceptable carriers as cosolvents for the acid base complex prepared in Example 1, the following experiments were performed.

2% by wt. of the complex formed in Example 1 was placed in aqueous solutions of a number of known carriers for pharmaceuticals. Table I lists the carrier concentrations which produced clear homogeneous solutions.

TABLE I 0.5% Polysorbate 80
1.0% Polysorbate 80
2.0% Polysorbate 80
0.5% Polysorbate 80 + 0.5% Polyethylene Glycol 400
0.5% Polysorbate 80 + 0.5% Polyethylene Glycol 40 stearate
1.4% Polyvinyl Alcohol + 0.5% Polysorbate 80
1.4% Polyvinyl Alcohol + 0.5% Polyethylene Glycol 400
1.4% Polyvinyl Alcohol + 0.5% Polyethylene Glycol 40 stearate
0.5% Polysorbate 80 + 0.5% Polyvinylpyrrolidone As illustrated in Example 2, polysorbates, polyethylene glycol stearates, polyethylene glycols, polyvinyl alcohols and polyvinylpyrrolidones are useful for dissolving the complexes of leukotriene receptor antagonists and antihistamines of the present invention. Polyethylene Glycol 40 Stearate and Polysorbate 80 are particularly suitable cosolvents. These solvents effectively dissolve compounds having lipophilic portions such as the leukotriene receptor antagonists and are water soluble. The amount of Polyethylene Glycol 40 Stearat and Polysorbate 80 which keeps the exemplary pharmaceutical compositions homogenous is small and varies with the amount of complex in the solution. For dilute solutions of the antihypersensitivity complexes, only small amounts of cosolvent are required and, therefore, very low viscosity pharmaceutical compositions are possible. Accordingly, aqueous solutions of 0.5% Polysorbate 80 containing as high as 2% by wt. complex of leukotriene receptor antagonist and antihistamine can be utilized in low viscosity formulations.

The pharmaceutical compositions of the present invention possess several advantageous features which make them particularly useful for treating hypersensitivity diseases. As mentioned above, the acid base complexes of leukotriene receptor antagonists and antihistamines provide single active compounds which have the unexpected beneficial effect of negating the tissue irritant properties associated with leukotriene receptor antagonists while retaining their pharmaceutical activity.

In addition to the nonirritating properties of the pharmaceutical compositions of the present invention attributed to the blocked carboxylates of the leukotriene receptor antagonist, the complexes are stable in solution and do not dissociate to the free acid and base when dissolved. This important property allows the pharmaceutical compositions of the present invention to be utilized in the preferred cosolvents without fear of disintegration or irritancy.

Further, the pharmaceutical compositions of the present invention also are stable at ambient conditions, and this stability remains true when the pharmaceutical compositions are incorporated into a pharmaceutically acceptable carrier. Thus, there is no need to refrigerate the acid-base complex or solutions of the complex as they retain their pharmacological activity even after prolonged storage at ambient temperatures and humidity.

Additionally, the pharmaceutical compositions of the present invention are sterilized easily using conventional sterile fill techniques. The acid-base complexes display no affinity for the filters used in sterilization processes and remain dissolved in aqueous based solutions containing the appropriate cosolvents during the filtration process. This stability facilitates the sterile fill process and reduces the associated expense.

Because the acid-base complexes utilized in the pharmaceutical compositions of the present invention are loose complexes of weak acids and weak bases, their activity and stability are pH dependent. Due to the relative strengths of both the acidic functionalities of the antihistamines and the basic functionalities of the leukotriene receptor antagonists, the complexes formed are nearly neutral. In fact the maximum stability of the pharmaceutical compositions of the present invention is at or near a pH of 7.4. This is significantly advantageous since 7.4 is the pH of most physiological fluids including that of the ocular tear film. Thus, the antihypersensitivity complexes of the present invention do not readily dissociate in physiologic fluids following application or delivery but remain relatively intact, slowly providing a continuously available nonirritating and active complex at the tissue site.

Additionally, the pharmaceutical compositions of the present invention are highly efficacious in their pharmacological activity. The combinations of leukotriene receptor antagonists and antihistamines which comprise the acid-base complexes have a synergistic effect in suppressing the symptoms of hypersensitivity diseases. Interactive Effects of Peptidoleukotrienes and Histamine on Microvascular Permeability and their Involvement in Experimental Cutaneous and Conjunctival Immediate Hypersensitivity, Eur. J. Pharmacol 164, 323–333, Woodward et al.) Thus, the pharmaceutical compositions of the present invention would display a greater ability toward suppressing the histaminergic and the nonhistaminergic component (mediated by peptidoleukotrienes) of hypersensitivity diseases than equal amounts of both a leukotriene receptor antagonist and an antihistamine administered separately.

This synergistic effect has been demonstrated by evaluating the ability of a leukotriene antagonist and an antihistamine to suppress ocular and cutaneous microvascular permeability in guinea pigs sensitized to chicken ovalbumin antigen. In such tests ocular and cutaneous microvascular permeability is associated with immediate hypersensitivity diseases and can be quantitatively determined as extravascular albumin accumulation. The following non-limiting examples illustrate the highly efficacious properties of the pharmaceutical composition against the major mediators of allergy (i.e. LTDs and histamine) prepared according to the teachings of the present invention.

EXAMPLE 3

Guinea pigs were inoculated in one eye with graded amounts of histamine and $LTD_4$, a leukotriene mediator. The other eye received equal volumes of saline control solutions. Prior to receiving the inoculation, the guinea pigs were topically pretreated with 20 μl of aqueous solutions of Polysorbate 80 and Polyethylene Glycol 40 Stearate containing 0.01 wt. % or 0.03 wt. % of the complex prepared in Example 1. Fifteen minutes following the inoculation the guinea pigs were sacrificed and their eyelids and bulbar conjunctivae were analyzed for extravascular albumin, an indicator of the degree of conjunctival microvascular permeability. The higher the amount of extravascular albumin, the more severe the symptoms of the disease.

Table II shows the effect of graded doses of LTD₄ in the presence and absence of 0.01 wt. % complex of the complex prepared in Example 1. It should be noted that the extravascular albumin is significantly decreased when the doses of LTD₄ are combined with a pharmaceutical composition of the present invention. Even when challenged with 100 ng of LTD₄ there is a marked and statistically significant decrease in permeability in eyes pretreated with 0.01% of the complex described in the present invention.

TABLE II 0.01% complex of 2(S)-hydroxy3(R)-{(2-carboxy-ethyl)thiol-3-[-2-(8-phenyloctyl)phenyl]propionic acid and pyrilamine

| DOSE LTD₄ DOSE OF LTD₄ | CONTROL-extra vascular albumin (ml/g) | | COMPLEX-extra vascular albumin (ml/g) | |
|---|---|---|---|---|
| | LIDS | BULBAR CONJUNCTIVAE | LIDS | BULBAR CONJUNCTIVAE |
| 1 ng | 0.29 ± 0.02 | 1.46 ± 0.12 | 0.23 ± 0.01* | 1.18 ± 0.25 |
| 10 ng | 0.38 ± 0.03 | 1.97 ± 0.26 | 0.31 ± 0.06 | 1.05 ± 0.18* |
| 100 ng | 0.56 ± 0.07 | 2.34 ± 0.17 | 0.51 ± 0.05 | 1.84 ± 0.15* |

*$P < 0.05$

Table III shows the effect of graded doses of LTD₄ in the presence or absence of 0.03 % by wt. of the complex prepared in Example 1. Even when challenged with 100 ng of LTD₄ there is a 33% decrease in albumin in the eyelids and a 44% decrease in the albumin in the bulbar conjunctiva.

TABLE III 0.03% complex of 2(S)-hydroxy3(R)-{(2-carboxy-ethyl)thiol-3-[-2-(8-phenyloctyl)phenyl]propionic acid and pyrilamine

| DOSE LTD₄ | CONTROL-extra vascular albumin (ml/g) | | COMPLEX-extra vascular albumin (ml/g) | |
|---|---|---|---|---|
| | LIDS | BULBAR CONJUNCTIVAE | LIDS | BULBAR CONJUNCTIVAE |
| 1 ng | 0.30 ± 0.02 | 1.33 ± 0.13 | 0.20 ± 0.01* | 0.89 ± 0.11* |
| 10 ng | 0.33 ± 0.06 | 1.44 ± 0.25 | 0.18 ± 0.04* | 0.71 ± 0.25* |
| 100 ng | 0.64 ± 0.04 | 2.46 ± 0.20 | 0.41 ± 0.03* | 1.37 ± 0.14* |

*$P < 0.05$

Table IV shows the effect of graded doses of histamine in the presence or absence of 0.03% by wt. of the complex prepared in Example 1. Even when challenged with 100 μg of histamine, there is a 77% decrease in albumin content in the eyelids and a 65% decrease in the albumin content in the bulbar conjunctiva.

TABLE IV 0.03% complex of 2(S)-hydroxy3(R)-{(2-carboxy-ethyl)thiol-3-[-2-(8-phenyloctyl)phenyl]propionic acid and pyrilamine

| DOSE histamine | CONTROL-extra vascular albumin (ml/g) | | COMPLEX-extra vascular albumin (ml/g) | |
|---|---|---|---|---|
| | LIDS | BULBAR CONJUNCTIVAE | LIDS | BULBAR CONJUNCTIVAE |
| 1 μg | 0.26 ± 0.03 | 2.52 ± 0.66 | 0.20 ± 0.01 | 0.78 ± 0.11 |
| 10 μg | 0.44 ± 0.06 | 2.74 ± 0.64 | 0.16 ± 0.01* | 0.67 ± 0.09* |
| 100 μg | 3.11 ± 0.24 | 6.49 ± 0.44 | 0.71 ± 0.08* | 2.27 ± 0.62* |

*$P < 0.05$

An associated method for treating hypersensitivity diseases in individuals suffering from these diseases comprises the steps of providing a complex of at least one leukotriene receptor antagonist and at least one antihistamine, and delivering a therapeutically effective amount of the complex to the individual to be treated. Furthermore, the complex can be incorporated into a pharmaceutically acceptable carrier to facilitate the delivery of the complex to selected tissue sites as desired.

For example, when the complex is incorporated in a pharmaceutically effective carrier having a high viscosity and very little added water, the resulting viscous formulation is readily administered as a topical cream to the ocular or cutaneous environment. Alternatively, the complex can be incorporated into low viscosity pharmaceutically effective carriers having large amounts of added water. The resulting low viscosity formulations are suitable for use as aerosols or injectable solutions. Aerosol applications of these compositions include use as nose sprays and bronchial inhalers while injectable solutions are suitable for both intramuscular, subcutaneous and IV applications.

Having thus described exemplary embodiments of the present invention, it should be noted by those skilled in the art that the disclosures herein are exemplary only and that alternatives, adaptations and modifications may be made with the scope of the present invention.

What is claimed is:

1. A pharmaceutical composition for topical application having enhanced effectiveness and decreased irritancy comprising a therapeutically effective amount of an acid-base complex of a leukotriene receptor antagonist and an antihistamine, said acid-base complex having the formula:

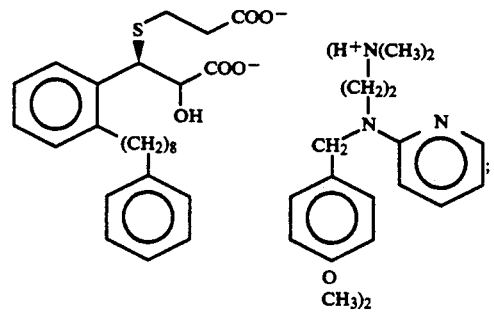

and a pharmaceutically acceptable carrier.

2. The pharmaceutical composition of claim 1 wherein said complex is present at a concentration of from approximately 0.001% by wt. to 10.0% by wt.

3. The pharmaceutical composition of claim 1 wherein said pharmaceutically acceptable carrier is selected from the group consisting of polysorbates, polyethylene glycols, polyethylene glycol stearates, polyvinylpyrrolidones and polyvinyl alcohols.

4. A method for treating immediate hypersensitivity diseases in individuals suffering therefrom, said method comprising:

topically administering a therapeutically effective amount of a complex of leukotriene receptor antagonist and an antihistamine, having the formula

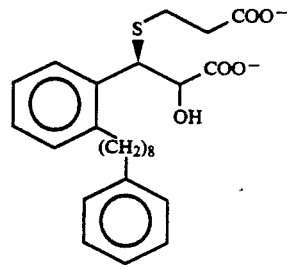
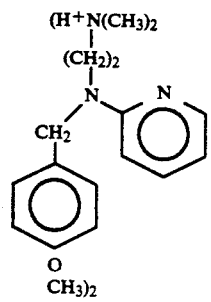

to an individual in need thereof.

5. The method of claim 4 wherein said complex is incorporated in a pharmaceutically acceptable topical carrier.

6. The method of claim 5 wherein said topical carrier is a high viscosity cream.

7. The method of claim 5 wherein said topical carrier is a low viscosity solution.

* * * * *